United States Patent [19]

Zajacek et al.

[11] Patent Number: 5,451,701
[45] Date of Patent: Sep. 19, 1995

[54] INTEGRATED PROCESS FOR CYCLOHEXANONE OXIME PRODUCTION

[75] Inventors: John G. Zajacek, Devon; John C. Jubin, West Chester, both of Pa.; Guy L. Crocco, Wilmington, Del.

[73] Assignee: Arco Chemical Technology, L.P., Greenville, Del.

[21] Appl. No.: 266,820

[22] Filed: Jun. 27, 1994

Related U.S. Application Data

[63] Continuation-in-part of Ser. No. 212,452, Mar. 11, 1994, abandoned.

[51] Int. Cl.$^6$ .................. C07C 249/04; C07D 201/02; C07D 201/04; C07D 201/06
[52] U.S. Cl. ................................ 564/267; 540/335; 540/336
[58] Field of Search ................ 540/535, 536; 564/267

[56] References Cited

U.S. PATENT DOCUMENTS

| | | | |
|---|---|---|---|
| 4,745,221 | 5/1988 | Roffia et al. | 564/267 |
| 4,749,198 | 12/1988 | Roffia et al. | 564/267 |
| 4,894,478 | 1/1990 | Roffia et al. | 564/267 |
| 5,041,652 | 8/1991 | Padovan et al. | 564/267 |

FOREIGN PATENT DOCUMENTS

| | | |
|---|---|---|
| 0267362 | 5/1988 | European Pat. Off. |
| 0434255 | 2/1968 | Japan |

OTHER PUBLICATIONS

G. Centi & F. Trifiro (Editors), New Developments in Selective Oxidation ©1990 Elsevier Science Publishers B.V. Amsterdam pp. 43–52.

A. J. H. P. van der Pol & J. H. C. van Hooff, Applied Catalysis A: General 106 (1993) pp. 97–113.

Paolo Raffia et al, A New Process for Cyclohexanone 1989, pp. 598–603.

J. Sudhakar Reddy, S. Swasanker, & P. Ratnasamy, Ammoximation of Cyclohexanone Over a Titanium Silicate Molecule Sieve TS-Z (1991) pp. 383–393.

M. Guesnet et al (Editors), Catalytic Oxidation with Hydrogen Peroxide: New & Selective Catalysts pp. 21–34, date 1993.

Ugo Romano et al, Selective Oxidation With Ti-Silicate Sep. 1989, pp. 610–616.

Primary Examiner—Peter O'Sullivan
Attorney, Agent, or Firm—Stephen D. Harper

[57] ABSTRACT

An integrated process for producing cyclohexanone oxime, a caprolactam precursor, is provided wherein a secondary alcohol is utilized to generate the hydrogen peroxide oxidizing agent and as a reaction medium for ammoximation. The ketone produced as a co-product is recycled back to the secondary alcohol by hydrogenation.

12 Claims, 1 Drawing Sheet

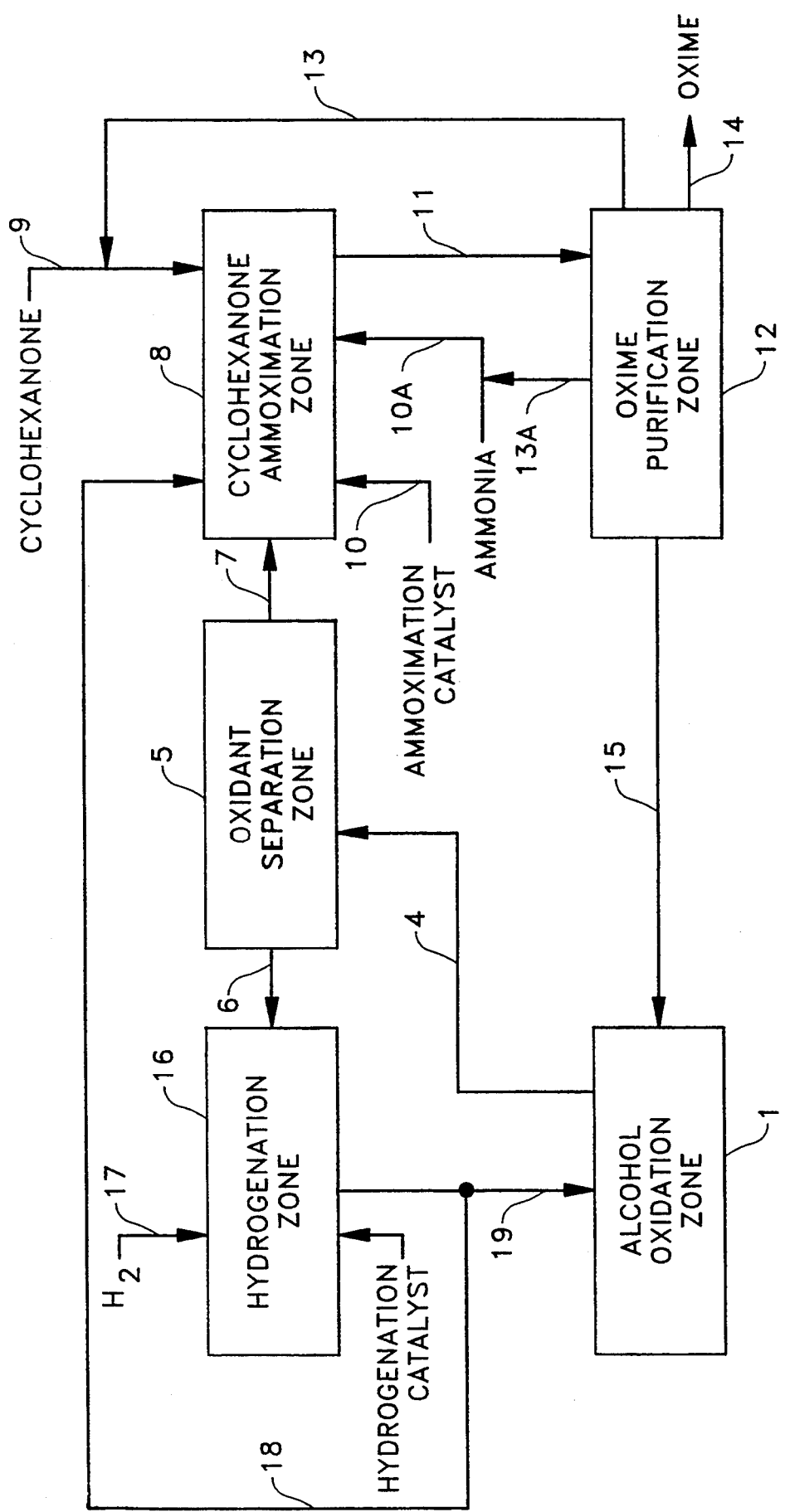

INTEGRATED PROCESS FOR CYCLOHEXANONE OXIME PRODUCTION

This is a continuation-in-part of application Ser. No. 08/212,452, filed Mar. 11, 1994, now abandoned.

FIELD OF THE INVENTION

This invention relates to an efficient method for obtaining cyclohexanone oxime wherein oxime is the sole major organic product.

BACKGROUND OF THE INVENTION

Caprolactam, which is employed in the production of nylon-6, may be derived from cyclohexanone oxime via an acid-catalyzed Beckmann rearrangement. At the present time, commercial processes for producing cyclohexanone oxime include the reaction of cyclohexanone with hydroxylamine sulfate and ammonia. Such a process is not ideal since it generates sulfate salt by-products and requires numerous steps. Improved procedures for producing cyclohexanone oxime therefore would be highly desirable.

SUMMARY OF THE INVENTION

The invention furnishes an integrated process for producing cyclohexanone oxime wherein a secondary alcohol such as isopropanol or sec-butanol is reacted with molecular oxygen in a liquid phase at a temperature of from 50° C. to 200° C. to form an oxidant mixture comprised of 40 to 90 weight percent of the secondary alcohol, 5 to 35 weight percent of a ketone corresponding to the secondary alcohol, 1 to 20 weight percent hydrogen peroxide, and 0 to 35 weight percent water. Substantially all of the ketone is separated from the oxidant mixture so as to provide a hydrogen peroxide-containing stream essentially free of ketone (e.g., less than 1 wt. %) and ketone peroxides (e.g., less than 0.5 wt. %). The ketone separated from the oxidant mixture is reacted with hydrogen in the presence of a heterogeneous hydrogenation catalyst wherein said catalyst is comprised of a transition metal selected from nickel, chromium, platinum, ruthenium, rhodium, and palladium at a temperature of from 20° C. to 175° C. and a hydrogen pressure of from 0.5 to 100 atmospheres. The ketone is thereby converted back to the corresponding secondary alcohol; the secondary alcohol obtained by hydrogenation is recycled for further use in generating additional quantities of hydrogen peroxide. The hydrogen peroxide-containing stream which is comprised of hydrogen peroxide and secondary alcohol but less than 1 weight percent ketone, is utilized as a source of hydrogen peroxide in the reaction of cyclohexanone with ammonia to form the desired cyclohexanone oxime product. A titanium silicalite catalyst serves to catalyze the cyclohexanone reaction. The secondary alcohol present in the ammoximation reaction product is recovered by a suitable means such as distillation and recycled back to the oxidation step of the process.

One key advantage of the process of this invention is that selectivity to cyclohexanone oxime is greatly enhanced by removing the ketone corresponding to the secondary alcohol from a hydrogen peroxide-containing oxidant mixture prior to use of that mixture in cyclohexanone ammoximation, since that ketone will itself undergo ammoximation, thereby consuming hydrogen peroxide. Separation of the ketone from the oxidant mixture has also been found to minimize the accumulation of organic peroxy species through the interaction of ketone and hydrogen peroxide. Moreover, such removal has been found to be effective in liberating hydrogen peroxide from any ketone peroxide generated during oxidation of the secondary alcohol or subsequent storage. Such peroxy species lower the overall efficiency of the process since hydrogen peroxide is being consumed and may complicate the purification or separation steps. Organic peroxides derived from acetone and hydrogen peroxide are known to be dangerously explosive (see, for example, Milas et al., *J. Am. Chem. Soc.* 81, 6461–6462 (1959)). Such ketone peroxides will tend to accumulate during secondary alcohol oxidation, during storage of the oxidate mixture, as well as during cyclohexanone ammoximation. In this context, the term "ketone peroxides" includes those organic compounds derived from interaction of the ketone and hydrogen peroxide which contain at least one —O—O— group (see for example, Sauer et al., *Physical Chem.* 75, 3004–3011 (1971) and Sauer et al., ibid. 76, 1283–1288 (1972)).

The ketone which is separated from the oxidant mixture may be readily transformed back to secondary alcohol by hydrogenation; the instant process thus is highly efficient since no substantial quantities of organic co-products are generated. Moreover, the only co-product which is produced (water) may be readily disposed of without significant environmental impact. The net overall reaction may be represented as follows:

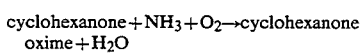

$$\text{cyclohexanone} + NH_3 + O_2 \rightarrow \text{cyclohexanone oxime} + H_2O$$

wherein the oxime is the only organic species produced (other than minor quantities of by-products) and cyclohexanone is the only organic species consumed.

Another surprising aspect of the process of the invention is that high selectivity to cyclohexanone oxime is attained in spite of the fact that substantial amounts of secondary alcohol are present during ammoximation. The prior art teaches that primary and secondary alcohols such as isopropanol are readily oxidized to the corresponding aldehydes and ketones by reacting with hydrogen peroxide in the presence of titanium silicalite (U.S. Pat. No. 4,480,135; a highly selective conversion of isopropanol to acetone is reported in Example 7). It has now been discovered that only minimal oxidation of secondary alcohol to the corresponding ketone takes place during ammoximation, despite the fact that both ketone and alcohol are known to react with hydrogen peroxide in the presence of titanium silicalite and thus would be expected to compete for the available active oxygen. The finding that nearly all of the hydrogen peroxide reacts selectively with the cyclohexanone substrate and not with the secondary alcohol was thus quite unexpected.

An additional unexpected finding was the discovery that, while it is critical to remove substantially all of the ketone by-product from the oxidant mixture prior to ammoximation, no other treatment or processing is necessary to reduce the levels of other by-products such as organic acids formed during secondary alcohol oxidation in order to realize high yields of cyclohexanone oxime.

Another advantage of the instant process is that the aliphatic secondary alcohol which serves as a reaction medium and also a source of hydrogen peroxide is relatively low boiling and thus considerably easier to separate from the cyclohexanone oxime product by distillative means than the aromatic secondary alcohols such as alpha methyl benzyl alcohol and anthrahydroquinone which have previously been suggested for use as solvent/hydrogen peroxide sources in titanium silicalite catalyzed oxidations.

BRIEF DESCRIPTION OF THE DRAWING

FIG. 1 illustrates in schematic form a suitable embodiment of the process of the invention.

DETAILED DESCRIPTION OF THE INVENTION

Isopropanol or sec-butanol is reacted with molecular oxygen from a suitable source such as air to yield an oxidant mixture. The secondary alcohol to be oxidized may contain minor amounts of the corresponding ketone and/or water. For example, the azeotropes of water and isopropanol or water and 2-butanol may be advantageously used. Methods of oxidizing secondary alcohols with molecular oxygen so as to obtain mixtures of hydrogen peroxide, ketone, and secondary alcohol are well-known in the art and are described, for example, in U.S. Pat. Nos. 2,819,949, 2,871,102, 2,871,103 and 2,479,111, and British Pat. Nos. 758,907, and 1,421,499 the teachings of which are incorporated herein by reference in their entirety. The reaction is preferably carried out in the liquid phase at a temperature of from 50° to 200° C. (more preferably, from 100° to 180° C.). Only partial conversion of the secondary alcohol (e.g., about 5 to 50%) is achieved. The unreacted secondary alcohol functions as a carrier or solvent for the hydrogen peroxide, ammonia, and cyclohexanone during ammoximation. Residence, hold-up, or reaction times of from about 0.25 to 4 hours will typically be sufficient for this purpose. The preferred range of oxygen partial pressure in the feed gases (which may include an inert diluent gas such as nitrogen in addition to oxygen) is 5 to 500 psia (more preferably, 15 to 250 psia) partial pressure. The hydrogen peroxide generated remains, collects, or accumulates in the liquid body comprised of secondary alcohol (water may also be present) that is undergoing oxidation. A small amount of hydrogen peroxide, organic peroxide or hydroperoxide can be used in the initial oxidation reaction mixture, particularly when a highly purified secondary alcohol is utilized as a feed. Although this secondary alcohol oxidation does not require the presence of an added catalyst, such a catalyst may be used if so desired as disclosed, for example, in U.S. Pat. No. 2,910,415 and British Pat. No. 871,830 (the teachings of which are incorporated herein by reference in their entirety). Materials which promote the decomposition of the hydrogen peroxide produced should be scrupulously excluded from the reaction zone within which the oxidation is conducted. Hydrogen peroxide stabilizers may be added, although care should be taken to avoid substances which may inhibit or otherwise detrimentally affect the subsequent ammoximation reaction. For example, high levels of certain alkali metal pyrophosphates have been found to poison the titanium silicalite ammoximation catalyst. The oxidant mixture generated by reacting the secondary alcohol will typically contain about one equivalent of hydrogen peroxide and one equivalent of ketone for every equivalent of secondary alcohol which has been consumed. Such a mixture thus will usually have the following composition: 40–90 weight % unreacted secondary alcohol, 5 to 35 weight % ketone, 1 to 20 weight % hydrogen peroxide, and 0 to 35 weight % water. The secondary alcohol oxidation can be carried out continuously (using, for instance, a continuous stirred tank reactor) or batchwise. A plurality of oxidation reaction zones maintained at different temperatures may be employed as described in British Pat. No. 758,907.

Prior to use of the oxidant mixture in the ammoximation step of this invention, it is critical that the ketone is substantially separated or removed from the oxidant mixture. Any known separation method or technique which is suitable for this purpose may be utilized, including fractionation procedures.

Preferably, however, the oxidant mixture is subjected to fractional distillation (preferably as soon as is practical following secondary alcohol oxidation so as to minimize the formation of ketone peroxide) whereby the liquid ketone in the mixture is converted into gaseous form by application of heat and/or reduced (subatmospheric) pressure and removed from the oxidant mixture as an overhead stream. The distillation conditions are selected such that while essentially all of the ketone is removed, the other components of the oxidant mixture are largely retained in the bottoms fraction and not taken overhead. In particular, it is highly desirable to avoid distilling out more than about 5% of the hydrogen peroxide present initially in the oxidant mixture in order to avoid possible explosion hazards and to preserve a satisfactorily high concentration of hydrogen peroxide (which will function as an oxidizing agent in the subsequent ammoximation step) in the bottoms fraction. The ketone should be substantially removed from the oxidant mixture as quickly as possible so that formation of organic peroxy species from interaction of the ketone and hydrogen peroxide is minimized. The oxidant mixture thus is preferably subjected to distillation immediately following molecular oxygen oxidation of the secondary alcohol. For example, the oxidant mixture stream coming out of the secondary alcohol oxidizer is preferably delivered directly into a distillation section and the ketone quickly flashed off to provide a bottoms fraction stream essentially free of the ketone. The ketone concentration in the resulting bottoms fraction should be less than 1 weight percent, more preferably, less than 0.5 weight percent. Intervening storage or retention of the oxidant mixture prior to distillation thus is avoided in preferred embodiments of this invention. To facilitate rapid and complete separation of the ketone from the oxidant mixture, it may be desirable to remove at the same time a portion of the secondary alcohol and/or water. For example, the overall composition of the overhead stream may be 30 to 100 weight % ketone, 0 to 70 volume % secondary alcohol and 0 to 30 volume % water. Since the ketone is recycled back to secondary alcohol by hydrogenation, the presence of some secondary alcohol in the overhead stream is not detrimental to the successful operation of the process of this invention. For safety reasons care must be taken not to overly concentrate the hydrogen peroxide in the bottoms fraction nor to have any appreciable concentration of hydrogen peroxide in the overhead stream. The residence time in the distillation step is also critical. The residence time must be sufficient to accomplish substantial reversal of any ketone/hydrogen peroxide reaction products generated during molecular oxygen oxidation or thereafter to bring the level of ketone peroxides to less than 0.5 weight percent total. Excessive residence time should be avoided, however, to avoid decomposition of the hydrogen peroxide. In one preferred embodiment of the invention, a residence time of 10 to 45 minutes (more preferably, 15 to 30 minutes) at 90° C. to 130° C. (more preferably, 100° C. to 120° C.) is employed. It has been unexpectedly found that the aforedescribed fractionation of the oxidant mixture may be readily achieved with minimal loss of hydrogen peroxide in the bottoms fraction through thermal decomposition, reaction with ketone or distillation.

Other separation procedures capable of reducing the aliphatic ketone content of the oxidant mixture without significant loss of the hydrogen peroxide contained therein may also be used including, for example, absorption, countercurrent extraction, membrane separation, and the like.

Methods of converting aliphatic ketones such as acetone and 2-butanone to their corresponding secondary aliphatic alcohols by catalytic hydrogenation using a transition metal catalyst and hydrogen gas are well-known and are generally described, for example, in the following publications (incorporated herein by reference in their entirety): Freifelder, *Catalytic Hydrogenation in Organic Synthesis—Procedures and Commentary*, Wiley-Interscience (1978), Augustine, *Catalytic Hydrogenation Techniques and Applications in Organic Synthesis* M. Dekker (1965), Freifelder, *Practical Catalytic Hydrogenation: Techniques and Applications* Wiley-Interscience (1971), Kieboom, *Hydrogenation and Hydrogenolysis in Synthetic Organic Chemistry*, Delft University Press (1977), and Peterson, *Hydrogenation Catalysts*, Noyes Data Corp. (1977). The following publications (incorporated herein by reference in their entirety) provide examples of specific catalysts and reaction conditions capable of selectively and rapidly hydrogenating acetone to isopropanol: U.S. Pat. No. 2,999,075, U.S. Pat. No. 3,013,990, Jpn. Kokai 3-133,941 (*Chem. Abst.* 115: 255631s), Jpn. Kokai 2-279,643 (*Chem. Abst.* 114:142662p), Jpn. Kokai 3-141,235 (*Chem Abst.* 115:235194y), Jpn. Kokai 3-41,038 (*Chem. Abst.* 114:228366g), Jpn. Kokai 62-12, 729 (*Chem. Abst.* 107:6768f), and Jpn. Kokai 59-189,938 (*Chem. Abst.* 102:138489x). While optimum hydrogenation conditions will vary somewhat depending upon the particular metallic catalyst selected for use and may be readily ascertained by routine experimentation, generally speaking temperatures of from 20° to 175° C. and hydrogen pressures of from 0.5 to 100 atmospheres will suffice. Preferably, the molar ratio of $H_2$ to ketone is from about 1:1 to 4:1. Catalyst concentrations of from about 0.1 to 10 weight percent based on the weight of the overhead stream will generally be suitable. The amount of catalyst employed is preferably sufficient to permit weight hourly space velocities of from 0.1 to 10 grams of ketone per gram of catalyst per hour. The reaction conditions should be chosen so as to avoid substantial over-reduction of the ketone to alkane.

The transition metal in the hydrogenation catalyst is most preferably palladium, platinum, chromium (as in copper chromite, for example), rhodium, nickel, or ruthenium. If water is present in the overhead stream, the use of Raney nickel or molybdenum-promoted nickel is especially advantageous. The hydrogenation is suitably carried out in either a liquid or vapor phase.

The hydrogen peroxide-containing stream containing hydrogen peroxide and secondary alcohol, but little or no ketone, is reacted with cyclohexanone and ammonia using titanium silicalite as a catalyst. Reactions of this type are well known in the art and suitable conditions for carrying out such a synthetic transformation are described, for example, in U.S. Pat. No. 4,745,221, Roffia et al., "Cyclohexanone Ammoximation: A Breakthrough in the 6-Caprolactam Production Process", in *New Developments in Selective Oxidation*. Centi et al, eds., pp. 43–52 (1990), Roffia et al., "A New Process for Cyclohexanonoxime", *La Chimica & L'Industria* 72, pp. 598–603 (1990), U.S. Pat. No. 4,894,478, U.S. Pat. No. 5,041,652, U.S. Pat. No. 4,794,198, Reddy et al., "Ammoximation of Cyclohexanone Over a Titanium Silicate Molecular Sieve", *J. Mol. Cat.* 69, 383–392 (1991), European Pat. Pub. No. 496,385, European Pat. Pub. No. 384,390, Italian Pat. No. 1,227,463, Italian Pat. No. 1,228,575, and U.S. Pat. No. 4,968,842 (the teachings of the foregoing publications are incorporated herein by reference in their entirety). Suitable titanium silicalite catalysts for this purpose, which can be broadly described as porous crystalline molecular sieves containing Si, Ti, and, optionally, minor amounts of other metals (e.g., Al, B, Fe) in their framework structures are also well known and are described in the foregoing publications and also in the following publications, the teachings of which are incorporated herein by reference in their entirety: U.S. Pat. No. 4,410,501 (Taramasso et al.), U.S. Pat. No. 4,824,976 (Clerici et al.), U.S. Pat. No. 4,666,692 (Taramasso et al.), Thangaraj et al., *J. Catal.* 130, 1 (1991), Reddy et al., *Applied Catal.* 58, L-1 (1990), Reddy et al., *J. Catal.* 130, 440 (1991), Reddy et al., *Zeolites* 12, 95 (1992), Belgian Pat. Pub. No. 1,001,038 (Bellussi et al.), Huybrechts et al., *J. Mol. Catal.* 71,129 (1992), Huybrechts et al., *Catal. Letter* 8, 237 (1991), U.S. Pat. No. 4,656,016 (Taramasso et al.), U.S. Pat. No. 4,859,785 (Bellussi et al.), European Pat. Pub. No. 311,983 (Padovan et al.), European Pat. Pub. No. 132,550 (Saleh), U.S. Pat. No. 5,082,641 (Popa et al.), Clerici et al., *J. Catal.* 129, 159 (1991), Bellussi et al., *J. Catal.* 133, 220 (1992), Szostak, *Molecular Sieves-Principles of Synthesis and Identification*, pp. 250–252 (1989), and Notari, "Synthesis and Catalytic Properties of Titanium Containing Zeolites", *Innovation in Zeolite Materials Science,* Grobet et al., Eds., 413 (1988), Tuel et al., *Zeolites* 13, 357–364 (1993), Tuel et al., *Zeolites* 13, 454461 (1993), van der Pol et al., *Applied Catal. A: General* 92, 93–111 (1992), Sulikowski et al, *Applied Catal A. General* 84, 141–153 (1992), Spanish Pat. Document No. 2,037,596 (Camblor et al.), U.S. Pat. No. 5,246,690 (Bellussi et al.), Dartt et al., "Synthesis and Physicochemical Properties of Zeolites Containing Framework Titanium", *Symposium on Chemically Modified Molecular Sieves,* presented before the Division of Petroleum Chemistry, Inc. 206th National Meeting, American Chemical Society, Chicago, Ill., Aug. 22–27, 1993, Camblor et al., *Zeolites,* 13, 82–87 (1993), Camblor et al, *J. Chem Soc. Chem. Commun,* 589–590 (1992), PCT International Publication No. WO 94/02245, French Pat. No. 2,694,549, and Kraushaar, *Catal. Lett.* 1, 81 (1988). Titanium silicalites are also at times referred to in the literature as titanium silicates and titanosilicalites.

Particularly preferred titanium silicalites include the classes of molecular sieves commonly referred to as "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Also suitable for use are the titanium-containing molecular sieves having framework structures isomorphous to zeolite beta which are described in U.S. application Ser. Nos. 08/172,404 and 08/172,405, filed Dec. 23, 1993. The titanium silicalite may contain minor amounts of metals other than titanium and silica in the lattice framework, such as, for example, aluminum, iron, boron, and the like.

Catalysts suitable for use in the process of this invention will have a composition corresponding to the empirical formula $xTiO_2$ $(1-x)SiO_2$, where x is between 0.0001 and 0.500. More preferably, the value of x is from 0.01 to 0.125. The use of silicalites containing a relatively high level of titanium i.e., where x is greater than 0.04) is especially advantageous. Such titanium-rich silicalite catalysts are described in Thangaraj et al., *J. Catal.* 130, 1 (1991), Thangaraj et al., *J. Chem. Soc. Chem. Commun.* 123 (1992) and Mira, Jkar et al., *J. Phys. Chem.* 96, 3073 (1992). The molar ratio of Si:Ti in the lattice framework of the titanium silicalite is advantageously from 9.5:1 to 99:1 (most preferably, from 9.5:1 to 70:1).

The titanium silicalite catalyst may be utilized in powder, pellet, extruded, microspheric, monolithic or any other suitable physical form. The use of a binder (co-gel) or support in combination with the titanium silicalite may be advantageous. The ammoximation is desirably performed at a temperature of from 25° C. to 150° C. (more preferably, 50° C. to 125° C.). The synthesis can be carried out either continuously or discontinuously, provided reactors are used whose surfaces are consistent with hydrogen peroxide. When the synthesis is carried out in batchwise fashion, it is advisable to use from 0.1 to 50 parts by weight (preferably from 1 to 20 parts by weight) of pure catalyst (binder excluded) for 100 parts by weight of cyclohexanone; if it is performed in a continuous mode, it is suggested to employ a space velocity from 0.1 to 100 kg/h of cyclohexanone ($C_6H_{10}O$) per kg of catalyst. The $H_2O_2$:$C_6H_{10}O$ molar ratio generally ranges from 0.5 to 2.5 and preferably from 0.8 to 1.5. The titanium silicalite may be preactivated by treating with hydrogen peroxide, as described in U.S. Pat. No. 4,794,198.

The ammonia is preferably added before the hydrogen peroxide, preferably in molar excess relative to the quantity of cyclohexanone (generally, at least 1.5 moles of ammonia per mole of cyclohexanone). Reaction times for the ammoximation preferably range from about 0.25 to 12 hours. The titanium silicalite catalyst can be arranged on a fixed bed or can be finely dispersed or suspended in the reaction medium. Suitable reactors in which the ammoximation may be conducted include isothermal slurry reactors, transport bed reactors, continuous stirred tank reactors and adiabatic trickle-bed reactors. The catalytic converter described in U.S. application Ser. No. 08/171,144, filed Dec. 20, 1993, may also be adapted for use. The reaction may be carried out at atmospheric pressure or, preferably, at a somewhat higher pressure in order to keep a quantity of ammonia at least equal to that required for the ammoximation dissolved in the reaction medium.

The use of a co-solvent (i.e., a solvent other than isopropanol, sec-butanol, or water) may under certain circumstances be advantageous in optimizing reaction rates or selectivity to oxime. Tertiary butyl alcohol is particularly suitable for this purpose.

At the end of the ammoximation reaction, which typically is carried out such that a high degree of cyclohexanone conversion (e.g., over 75%) is achieved, the cyclohexanone oxime can be separated and purified by any suitable material such as, for example, extraction or distillation or may, if desired, be directly converted without isolation to caprolactam using known procedures such as sulfuric acid-catalyzed rearrangement. A vapor phase Beckmann rearrangement of the cyclohexamine oxime catalyzed by titanium silicalite, as described in Thangaraj et al., *J. Catalysis* 37, 252–256 (1992) could also be practiced. The secondary alcohol may be recovered from the ammoximation reaction product by any appropriate method such as fractional distillation or the like and recycled for use in the molecular oxygen oxidation step of the instant process. Water is generated as a coproduct in the process of this invention and may be recycled together as an azeotrope with the secondary alcohol to the molecular oxygen oxidation step of the process. Any water present in excess of the quantity removable as a secondary alcohol azeotrope may be removed by distillation from the cyclohexanone oxime following removal of the secondary alcohol/water azeotrope.

FIG. 1 illustrates one embodiment of the integrated ammoximation process of this invention wherein cyclohexanone is converted to cyclohexanone oxime. Streams comprised of secondary alcohol pass via lines 15 and 19 into alcohol oxidation zone 1 wherein isopropanol or sec-butanol is reacted with molecular oxygen to form an oxidant mixture comprised of hydrogen peroxide, the ketone corresponding to the secondary alcohol, and excess secondary alcohol. The molecular oxygen may be provided by air, pure oxygen, or a synthetic mixture of $O_2$ and an inert gas such as nitrogen introduced via line 2.

The oxidant mixture containing hydrogen peroxide passes from zone 1 via line 4 into oxidant separation zone 5. In 5, the oxidant mixture is subjected to fractional distillation or other such separation procedure capable of removing ketone from the mixture. Ketone (and, optionally, a portion of the secondary alcohol and/or water, but little or no hydrogen peroxide) may be for example, be taken overhead into hydrogenation zone 16 via line 6. The overhead stream exiting zone 5 in gaseous form may be condensed into liquid form prior to or upon entering zone 16; alternatively, the overhead stream may be maintained in gaseous form while being hydrogenated (i.e., a vapor phase hydrogenation may be performed). The bottoms hydrogen peroxide-containing stream from zone 5, which may be a bottoms fraction and which contains hydrogen peroxide and most of the secondary alcohol but essentially no ketone or ketone peroxides, is introduced via line 7 into cyclohexanone ammoximation zone 8.

The cyclohexanone to be ammoximated is fed into ammoximation zone 8 via line 9, while the titanium silicalite catalyst is introduced via line 10. Alternatively, the titanium silicalite may be deployed in zone 8 as a fixed bed. Ammonia may be introduced to zone 8 via line 10A or, if desired, via line 9 in admixture with cyclohexanone. The resulting reaction mixture is maintained at the desired temperature and pressure in zone 8 for a time sufficient to convert at least a portion, and preferably at least about 75% of the cyclohexanone to cyclohexanone oxime, thereby consuming a portion of the hydrogen peroxide (which is converted to water). Preferably, substantially all of the hydrogen peroxide (e.g., at least 90%, most preferably, at least 98%) is reacted. The crude ammoximation product thus generated passes through line 11 to oxime purification zone 12 where it is separated by fractional distillation or other such means into a recycled cyclohexanone stream (returned to cyclohexanone feed line 9 or ammoximation zone 8 via line 13), an ammonia stream containing excess or unreacted ammonia (returned to ammonia feed line 10A via line 13A), an oxime stream containing the desired cyclohexanone oxime product (withdrawn via line 14), and an alcohol stream comprised of an azeotrope of water and the secondary alcohol which served as a reaction medium and hydrogen peroxide carrier during ammoxidation (withdrawn via line 15). Any water in excess of the amount removable by azeotrope distillation may be also separated as a distinct fraction during distillation. For example, it will be generally desirable to remove that portion of the water generated as an ammoxidation co-product in excess of that present in a secondary alcohol/water azeotrope so that the water content in the ammoxidation reaction mixture does not continue to increase through successive cycles of the process. The alcohol stream is returned to alcohol oxidation zone 1 via line 15. Alternatively, crude ammoxidation product is treated so as to convert the cyclohexanone oxime present to caprolactam and the other components present (such as, for example, secondary alcohol and water) thereafter separated from the caprolactam by appropriate means such as distillation. Partial fractionation of the crude ammoxidation product prior to oxime rearrangement is also possible. The boiling point of the various likely components of the crude ammoxidation product and caprolactam (which is obtainable by rearrangement of the cyclohexanone oxime) are as follows and are sufficiently distinct so as to permit facile separation by distillative means:

| Component | Boiling Point, °C. (pressure) |
|---|---|
| isopropanol/water | 80.4 (1 atm.) |
| sec-butanol/water | 88.5 (1 atm.) |
| cyclohexanone | 155 (1 atm.) |
| cyclohexanone oxime | 206–210 (1 atm.) |
| caprolactam | 136–138 (10 mm Hg) |

If any unreacted hydrogen peroxide is present in the crude ammoxidation reaction product, it may either be removed in the form of an aqueous or organic solution or decomposed by some suitable method. The recovered titanium silicalite may be returned to ammoxidation zone 8 via line 10; regeneration or other treatment of all or a portion of the catalyst may advantageously be performed at this point. Alternatively, the titanium silicalite may be recovered by an appropriate means such as filtration from the crude ammoxidation reaction product prior to separation of any of the other components thereof.

The ketone separated from the oxidant mixture (which may be in the form of an overhead stream) is passed via line 6 to hydrogenation zone 16 wherein the stream is reacted with hydrogen ($H_2$) introduced via line 17 in the presence of a suitable transition metal hydrogenation catalyst (introduced via line 18 or deployed as a fixed bed in zone 16) so as to convert at least a portion, and preferably substantially all, of the ketone present back to secondary alcohol. A portion of the hydrogenated stream exiting zone 16 may advantageously be fed to ammoxidation zone 8 via line 18 to dilute the hydrogen peroxide to the desired concentration; it is particularly desirable to practice this embodiment where a substantial proportion of alcohol has been removed together with the ketone from the oxidant mixture. The hydrogenated stream produced in zone 16 is passed via line 19 to alcohol oxidation zone 1. This integrated process is preferably operated in a continuous manner such that the desired cyclohexanone oxime is the only major organic product and the ketone and secondary alcohol are recycled through multiple cycles.

From the foregoing description, one skilled in the art can readily ascertain the essential characteristics of this invention, and, without departing from the spirit and scope thereof, can make various changes and modifications of the invention to adapt it to various usages, conditions, and embodiments.

EXAMPLES

Example 1

Preparation of TS-1 Catalyst

A titanium silicalite TS-1catalyst was prepared by reacting tetraethylorthosilicate, titanium (IV) ethoxide, and tetrapropylammonium hydroxide in accordance with the procedures described in U.S. Pat No. 4,410,501. Crystallization was performed at 175° C. for 3 days. The resulting catalyst was washed 3 times with water, dried, and calcined at 550° C. for 5 hours. The calcined catalyst was subsequently washed 3 times with boiling 0.5% aqueous sodium acetate, 3 times with water, and then recalcined at 550° C. The Ti/Si ratio of the recalcined catalyst was found to be 0.018.

Example 2

Preparation of Activated TS-1 Catalyst

The procedure of Example 1 was repeated except that after drying the catalyst was calcined at 420° C. for 10 hours. The catalyst was thereafter washed 3 times with a boiling solution prepared by mixing 1000 mL of a 5% sulfuric acid solution and 100 mL of 30% hydrogen peroxide. The resulting catalyst was then washed 3 times with water, dried, and calcined at 550° C. for 5 hours. Preparation of the activated catalyst was in accordance with Example 2 of European Pat. Pub. No. 267,362.

Comparative Example 3

Attempted Ammoximation of Cyclohexanone Using Acetone-Containing Oxidant Mixture This comparative example illustrates the relatively poor results obtained if ammoximation of cyclohexanone is attempted using an air-oxidized isopropanol oxidant mixture which has not been treated to remove acetone.

Isopropanol (300 g in 50 g water) was oxidized in a 1 liter stainless steel autoclave equipment with an internal cooling coil and a sparge tube connected to air and nitrogen cylinders. The oxidation reaction was initiated with dicumyl peroxide at 135° C. and maintained at 135° C. with stirring for 5 hours at 800 psig and a constant oxygen partial pressure of greater than 5%. The resulting oxidant mixture was found to contain 7.0 weight % hydrogen peroxide by iodiometric titration and 16.0 weight % acetone by gas chromatography. Isopropanol conversion was 20%; selectivity to hydrogen peroxide was 75%.

A round bottom flask was charged with 1.0 g of activated TS-1 catalyst (prepared as in Example 2), 5.19 g (0.0526 mol) cyclohexanone, 19.6 g (0.17 mol) ammonium hydroxide (30%), and 27.1 g t-butyl alcohol. The flask was fitted with a reflux condenser and addition funnel and submerged in an oil bath. After heating the contents of the flask to 60° C., the oxidant mixture (32.7 g; 0.0673 mol $H_2O_2$) was added over 40 minutes. The reaction mixture was thereafter stirred for an additional 4 hours at 60° C. The product was iodiometrically titrated and analyzed by gas chromatography. Hydrogen peroxide conversion was 85%. While 42% selectivity to the desired cyclohexanone oxime was observed, a substantial quantity (38% selectivity) of acetone oxime was obtained as a by-product. Cyclohexanone conversion was 48%, with 96% selectivity to cyclohexanone oxime based on cyclohexanone.

Example 4

Ammoximation of Cyclohexanone Using Acetone-Free Isopropanol Oxidant Mixture

This example demonstrates the improved cyclohexanone oxime selectivity realized by practice of the process of this invention.

A round bottom flask was charged with 2.0 g of activated TS-1 catalyst (prepared as in Example 2), 8.83 g (0.0900 mol) cyclohexanone, 44.7 g (0.38 mol) ammonium hydroxide (30%), and 9.59 g t-butyl alcohol. After fitting with a reflux condenser and addition funnel, the flask was submerged in an oil bath. After heating the contents of the flask to 60° C., 32.65 g of an acetone-free hydrogen peroxide solution similar to that obtainable by removing acetone by distillation from an air-oxidized isopropanol oxidant mixture was added over 30 minutes. The acetone-free hydrogen peroxide solution contained 9.59 weight % hydrogen peroxide, ca. 10 weight % water, ca. 0.2 weight % acetic acid, and ca. 0.05 g formic acid, the balance being isopropanol. The reaction product was stirred an additional 4 hours at 60° C. after addition of the acetone-free hydrogen peroxide solution was completed, then cooled and filtered. The organic and aqueous layers were separated and the aqueous layer washed with 3×30 mL toluene. The organic layers were combined and analyzed by gas chromatography for cyclohexanone, cyclohexanone oxime, acetone, and acetone oxime. The aqueous layer was iodometrically titrated for hydrogen peroxide and also analyzed by gas chromatography for organic products.

Significantly greater selectivity to cyclohexanone oxime based on hydrogen peroxide was observed (Table I) as a result of using a hydrogen peroxide source free of acetone than in Comparative Example 3.

Example 5

Example 4 was repeated using 2.0 g activated TS-1 catalyst, 9.87 g (0.101 mol) cyclohexanone, 38.8 g (0.32 mol) of 30% ammonium hydroxide, 38.7 g t-butyl alcohol, and 22.2 g of acetone-free isopropanol oxidant mixture (10.9 weight % $H_2O_2$; 0.0711 mol). After filtration, the reaction product was one phase. The product was iodometrically titrated and analyzed by gas chromatography. A high yield of cyclohexanone oxime was again obtained (Table I).

Example 6

Example 5 was repeated using 1.0 g of activated TS-1 catalyst, 5.14 g (0.0524 mol) cyclohexanone, 22.4 g (0.19 mol) 30% ammonium hydroxide, 16.9 t-butyl alcohol, and 16.9 g of acetone-free isopropanol oxidant mixture (10.9% $H_2O_2$; 0.0542 mol). The results obtained are shown in Table I.

Example 7

Example 5 was repeated using 1.0 g of activated TS-1 catalyst, 5.16 g (0.0526 mol) cyclohexanone, 16.6 g (0.14 mol) 30% ammonium hydroxide, 53.1 g t-butyl alcohol, and 16.8 g of acetone-free isopropanol oxidant mixture (10.9% $H_2O_2$; 0.0538 mol). Table I shows the results obtained.

Example 8

Example 5 was repeated using 1.0 g of activated TS-1 catalyst, 5.14 g (0.0524 mol) cyclohexanone, 20.6 g (0.18 mol) 30% ammonium hydroxide, 34.2 g t-butyl alcohol, and 9.82 g of an acetone-free isopropanol oxidant mixture prepared by mixing 62 g isopropanol, 38 g 50% aqueous hydrogen peroxide, 0.20 g acetic acid, and 0.050 g formic acid (18.57% $H_2O_2$; 0.0536 mol). The results obtained are shown in Table I.

Example 9

Example 5 was repeated using 1.0 g of unactivated TS-1 catalyst prepared in accordance with Example 1, 5.17 g (0.0526 mol) cyclohexanone, 19.1 g (0.16 mol) 30% ammonium hydroxide, 28.5 g t-butyl alcohol, and 16.7 g of acetone-free isopropanol oxidant mixture (10.9 weight % $H_2O_2$; 0.0536 mol). Satisfactory yields of the desired cyclohexanone oxime were obtained even though an unactivated titanium silicalite was employed (Table I).

TABLE I

| | Example No. | | | | | |
|---|---|---|---|---|---|---|
| | 4 | 5 | 6 | 7 | 8 | 9 |
| % $H_2O_2$ Conversion | 96 | 99 | 92 | 96 | 96 | 94 |
| % Cyclohexanone Oxime Selectivity (based on $H_2O_2$) | 63 | 74 | 74 | 71 | 62 | 61 |
| % Acetone Selectivity (based on $H_2O_2$) | 1 | 7 | 3 | 2 | 0 | 1 |
| % Acetone Oxime Selectivity (based on $H_2O_2$) | 0 | 0 | 0 | 0 | 0 | 0 |
| % Cyclohexanone Conversion | 78 | 69 | 81 | 82 | 87 | 76 |
| % Cyclohexanone Oxime Selectivity (based on cyclohexanone) | 80 | 75 | 87 | 86 | 71 | 77 |

We claim:

1. An integrated process for producing cyclohexanone oxime comprising the steps of:
   (a) reacting a secondary alcohol selected from sec-butanol and isopropanol with molecular oxygen in a liquid phase at a temperature of from 50° C. to 200° C. to form an oxidant mixture comprised of 40 to 90 weight percent of the secondary alcohol, 5 to 35 weight percent of a ketone corresponding to the secondary alcohol, 1 to 20 weight percent hydrogen peroxide, and 0 to 35 weight percent water;
   (b) separating substantially all of the ketone from the oxidant mixture so as to provide a hydrogen peroxide-containing stream comprised of secondary alcohol, hydrogen peroxide, less than 1 weight percent ketone and less than 0.5 weight percent ketone peroxides,
   (c) reacting the ketone separated in step (b) with hydrogen in the presence of a heterogeneous hydrogenation catalyst wherein said hydrogenation catalyst is comprised of a transition metal selected from nickel, chromium, platinum, ruthenium, rhodium and palladium at a temperature of from 20° to 175° C. and a hydrogen pressure of from 0.5 to 100 atmospheres to convert the ketone to the corresponding secondary alcohol;
   (d) reacting cyclohexanone with ammonia and the hydrogen peroxide-containing stream at a temperature of from 25° C. to 150° C. in the presence of a catalytically effective amount of a titanium silicalite to form an ammoximation reaction product comprised of cyclohexanone oxime and secondary alcohol;

(e) recovering the secondary alcohol from the ammoximation reaction product; and (f) recycling at least a portion of the secondary alcohol produced in steps (c) and (e) for use in step (a).

2. The process of claim 1 wherein the secondary alcohol is isopropanol.

3. The process of claim 1 wherein the titanium silicalite has an MFI, MEL, or zeolite beta topology.

4. The process of claim 1 wherein the titanium silicalite has a composition corresponding to the chemical formula $xSiO_2:(1-x)TiO_2$ wherein x is from 0.01 to 0.125.

5. The process of claim 1 wherein said process is carried out continuously.

6. The process of claim 1 wherein the titanium silicalite is deployed in the form of a fixed bed.

7. The process of claim 1 comprising an additional step wherein the cyclohexanone oxime is converted to caprolactam.

8. The process of claim 7 wherein said additional step is performed after step (d) and before step (e).

9. The process of claim 1 wherein the heterogeneous hydrogenation catalyst is a Raney nickel catalyst.

10. The process of claim 1 wherein separation step (b) is accomplished by distillation whereby substantially all of the ketone is vaporized and removed from the oxidant mixture as an overhead stream.

11. The process of claim 1 wherein recovery step (e) is accomplished by fractional distillation.

12. A continuous integrated process for producing cyclohexanone oxime comprising the steps of:

(a) reacting isopropanol with molecular oxygen in a liquid phase at a temperature of from 100° C. to 180° C. and a partial oxygen pressure of from 15 to 250 psia to form an oxidant mixture comprised of 40 to 90 weight percent isopropanol, 5 to 35 weight percent acetone, 1 to 20 weight percent hydrogen peroxide and 0 to 35 weight percent water;

(b) subjecting the oxidant mixture to fractional distillation so as to remove substantially all of the acetone in vapor form as an overhead stream and to provide a bottom fraction comprised of isopropanol, hydrogen peroxide, less than 1 weight percent acetone and less than 0.5 weight percent acetone peroxides, (c) reacting the overhead stream with hydrogen in the presence of a heterogeneous hydrogenation catalyst wherein said hydrogenation catalyst is comprised of a transition metal selected from nickel and ruthenium at a temperature of from 20° to 175° C. and a molar ratio of hydrogen to acetone of from 1:1 to 4:1 to convert the acetone in the overhead stream to isopropanol;

(d) reacting cyclohexanone with a molar excess of ammonia and the bottoms fraction at a temperature of from 50° C. to 125° C. in the presence of a catalytically effective amount of a titanium silicalite having an MFI, MEL, or zeolite beta topology and corresponding to the chemical formula $xSiO_2:(1-x)TiO_2$ wherein x is from 0.01 to 0.125 to form an ammoximation reaction product comprised of cyclohexanone oxime and isopropanol;

(e) recovering the isopropanol from the ammoximation reaction product by distillation; and (f) recycling at least a portion of the isopropanol produced in step (c) and (e) for use in step (a).

* * * * *